ically treated to remove oxidants. This reagent may be used by itself or in conjunction with an assay reagent system for use in the clinical laboratory.

United States Patent [19]
Yost

[11] Patent Number: 4,704,365
[45] Date of Patent: Nov. 3, 1987

[54] COMPOSITION AND METHOD FOR STABILIZATION OF DINUCLEOTIDES

[75] Inventor: David A. Yost, Round Lake Park, Ill.

[73] Assignee: Abbott Laboratories, North Chicago, Ill.

[21] Appl. No.: 832,851

[22] Filed: Feb. 24, 1986

[51] Int. Cl.⁴ .................. G01N 31/00; C12N 9/96
[52] U.S. Cl. ............................. 436/18; 435/188; 436/8; 436/17
[58] Field of Search ..................... 436/8–19; 252/408.1; 435/92, 188, 194, 832; 536/27

[56] References Cited
U.S. PATENT DOCUMENTS 4,153,511 5/1979 Modrovich ............... 436/17
4,372,874 2/1983 Modrovich ............... 436/17

Primary Examiner—Deborah L. Kyle
Assistant Examiner—T. J. Wallen
Attorney, Agent, or Firm—Martin L. Katz; Alan W. Kowalchyk

[57] ABSTRACT

A reduced dinucleotide, preferably nicotinamide adenine dinucleotide (NADH), is stabilized in an aqueous base liquid containing propylene glycol, boric acid and a buffer capable of buffering within a pH range of 8–11. The stabilized liquid contains greater than 50% (v/v) water. The remaining volume contains propylene glycol which has been chemically treated to remove oxidants. This reagent may be used by itself or in conjunction with an assay reagent system for use in the clinical laboratory.

15 Claims, 4 Drawing Figures

NADH STABILITY

NADH STABILITY

COMPOSITION AND METHOD FOR STABILIZATION OF DINUCLEOTIDES

BACKGROUND

The present invention relates in general to methods and compositions for stabilizing coenzymes and in particular to methods and compositions for stabilizing NADH in solution.

Biochemical reactions are almost universally catalyzed by enzymes. Each enzyme is a protein which promotes a highly specific chemical change in a substrate.

In order for many kinds of enzymes to function, the participation of a type of low molecular weight molecule, called a coenzyme, is required. In general, a chemical change in a coenzyme counterbalances a change in a substrate which is the desired outcome of a reaction. For example, a coenzyme may accept a hydrogen ion from or donate a hydrogen ion to a substrate.

A number clinical of diagnostic assays involve oxidation-reduction reactions. Among these diagnostic reactions are those in which a dinucleotide acts as a coenzyme. Examples of such dinucleotides include nicotinamide adenine dinucleotide (NAD), nicotinamide adenine dinucleotide 2'-phosphate (NADP) and flavin adenine dinucleotide (FAD).

Dinucleotides are mononucleotides joined by a phosphate bridge. A mononucleotide is a phosphoric acid ester of nitrogenous base and a sugar. In NAD and NADP, a first mononucleotide is a phosphoric acid ester of a nucleoside formed from the base adenine and the sugar ribose, while a second mononucleotide is a phosphoric acid ester of a nucleoside formed from the base nicotinamide and ribose. In FAD, a first mononucleotide formed from a phosphoric acid ester of adenine and ribose is linked to a second mononucleotide formed from a phosphoric acid ester of the base 7,8-dimethylisoalloxazine and the sugar alcohol D-ribitol.

Either NAD or NADP may serve as an electron acceptor from a reduced substrate ($S_r$) by receiving a hydrogen with associated electrons or may serve as an electron donor to an oxidized substrate ($S_o$) in a reverse reaction, i.e.:

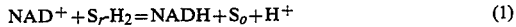
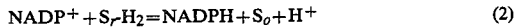

$$NAD^+ + S_r\text{-}H_2 = NADH + S_o + H^+ \quad (1)$$

$$NADP^+ + S_r\text{-}H_2 = NADPH + S_o + H^+ \quad (2)$$

A useful feature of these reactions is that the reduced forms of these dinucleotides (i.e., NADH and NADPH) absorb light at a wavelength of 340 nm, but the oxidized forms (i.e., $NAD_+$ and $NADP_+$) do not. Therefore, after plotting a calibration curve of reaction rate for a known quantity of enzyme, the unknown quantity of an enzyme catalyzing one of these reactions may be obtained from a given amount of substrate, a known activity for the enzyme and an observed rate of change in optical density at 340 nm. Likewise, the quantity of a substrate of an enzyme catalyzing one of these reactions may be determined from the calibration curve, a given amount of an enzyme of known activity and a measured rate of change in optical density at 340 nm.

Although valuable in diagnostic assays, NADH, like other reduced dinucleotides, is very unstable in aqueous solution. This presents a particular problem for the manufacturer of and for users of diagnostic assay kits inasmuch as it is much easier, cheaper and more accurate to dispense an aqueous solution of NADH than it is to dispense NADH in the more stable form of a dry powder.

One approach to stabilizing an NADH solution involves mixture with an organic solvent to eliminate as much water as possible. In U.S. Pat. No. 4,153,511, an inert, hygroscopic agent and an organic solvent are employed to obtain an NADH solution containing less than 0.5% water. However, NADH solutions in available non-aqueous solvents tend to be viscous to the point of being difficult to dispense accurately and precisely.

In another approach, coenzymes, such as NAD and NADP, are stabilized in the presence of an organic solvent, preferably a liquid polyol such as glycerol or propylene glycol, at an acidic pH. However, such solutions are relatively unstable and are particularly unsuitable for automated assays where virtually 100% stability of the reduced coenzyme is required.

SUMMARY OF THE INVENTION

A stabilized coenzyme composition according to the present invention includes: a basic, aqueous solution; a reduced dinucleotide, preferably NADH or NADPH, at a first concentration in the aqueous solution; a polyhydroxyl alkyl solvent, most preferably propylene glycol, in the aqueous solution; and a borate cis-hydroxyl binding compound, most preferably boric acid or a salt thereof, at a second concentration in the aqueous solution, the second concentration being about equal to or greater than the first concentration.

A currently preferred, stabilized coenzyme composition according to the present invention includes: an aqueous solution at a pH between about 8 and about 11; a Bicine buffer (N-N-bis [2-hydroxyethylglycine]) at a concentration within a range from about 10 mM to about 500 mM; NADH at a concentration within a range from about 0.001 mM to about 50 mM; boric acid at a concentration at least equal to the concentration of NADH and within a range from about 10 mM to about 500 mM; and propylene glycol at a concentration within a range from about 20% v/v to about 90% v/v of the aqueous solution. The most preferred coenzyme composition is one wherein the NADH is at a concentration of 10 mM, the boric acid is at a concentration of 50 mM, the propylene glycol is at a concentration of 50% v/v, and the Bicine buffer is at a concentration of 200 mM and is adjusted to about pH 10.0.

A method for stabilizing a solution of a reduced dinucleotide according to the present invention includes the steps of: dissolving a first concentration of a reduced dinucleotide in a basic aqueous solution; buffering the aqueous solution to a pH between about 8.0 and about 11.0; exposing the reduced dinucleotide to a borate cis-hydroxyl binding compound at a second concentration about equal to or greater than the first concentration; and reducing exposure of the reduced dinucleotide to water by making the aqueous solution from about 20% v/v to about 90% v/v in a polyhydroxyl alkyl solvent.

DETAILED DESCRIPTION

Figure 1:
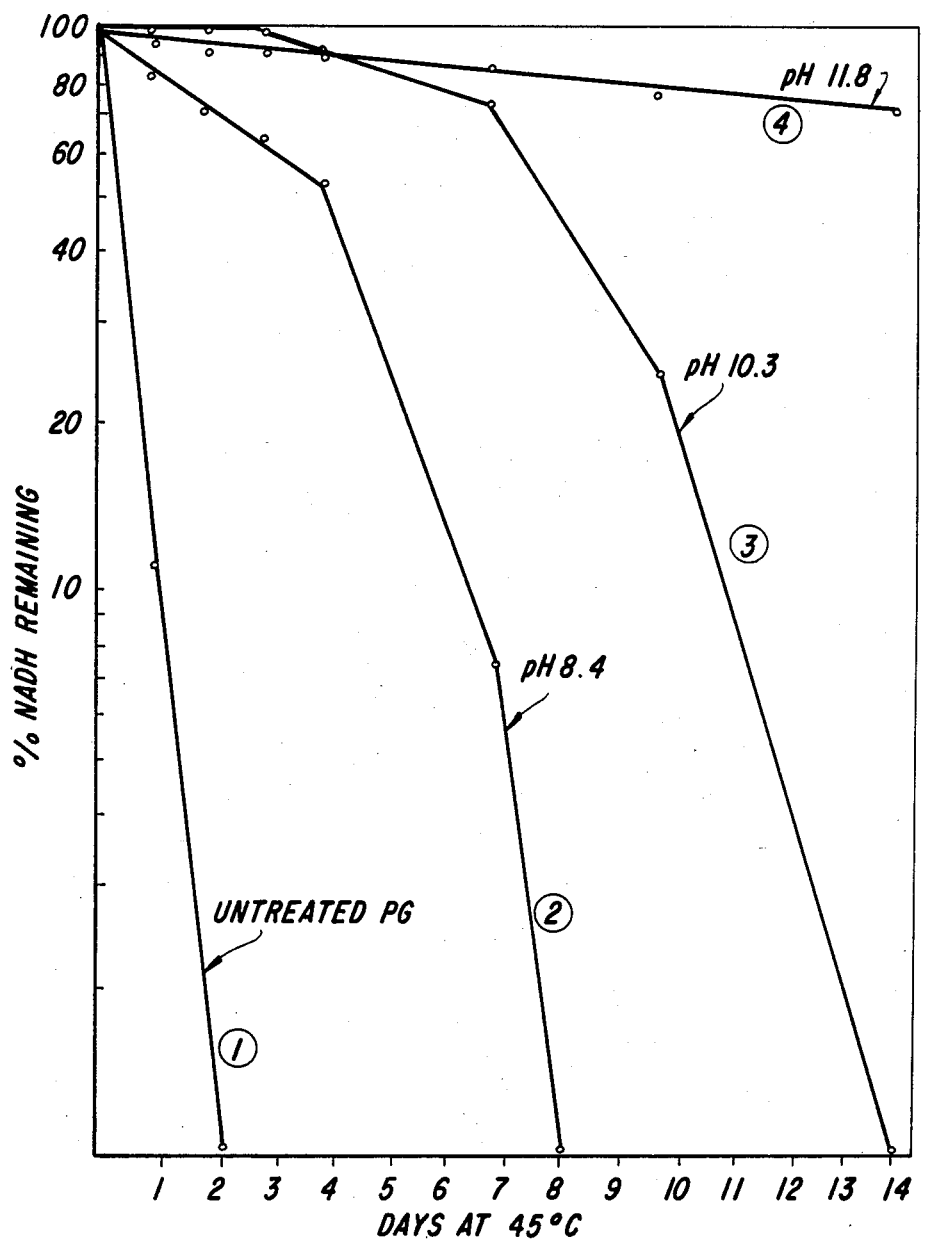
FIG. 1 is a graphic depiction of a comparison of the stability of NADH in metal-contaminated propylene glycol with the stability of NADH in uncontaminated propylene glycol at various pH values.

NADH is a coenzyme which has widespread use in clinical chemistry. Current formulations are usually dry filled or freeze dried and are unstable upon reconstitution. Dry formulations are prone to reagent waste during mixing by the customer. Moreover, manufacture of dry formulations involves expenses for freeze drying and dry blending. There is also a loss of quality control by the manufacturer when the customer must be relied upon to properly reconstitute a reagent.

The present invention involves the preparation and use of a highly stable, aqueous NADH solution. Presently available liquid NADH formulations are described as being essentially free of water and are difficult to pipette. By comparison with the present invention, these formulations are more expensive and their production is more labor intensive.

The present invention provides a solution of liquid NADH which is at least stable for about one year. This solution may be used in systems wherein the oxidation of NADH is employed for the determination of analyte concentrations. The loss of NADH may be determined: directly by the loss of absorbance in the 340 nm region, or the loss in a coupled colorimetric system; fluorometrically; or electrochemically. The use of an aqueous NADH solution provides greater flexibility then total organic solution previously made. One advantage of the present invention over NADH solutions which exclude water is the ability to make measurements of NADH which depend upon the presence of a conductive solution.

Although NADH has been bound to affinity chromatography columns having boronate binding groups, eluted with a sodium borate solution and the eluate examined spectrophotometrically for the presence of NADH [Maestas et al., *J. Chromatogr.*, 189, 225–231 (1980)], no suggestion has heretofor been presented that NADH is especially stable in such an eluate or that addition of an organic solvent to such an eluate would result in a particularly stable coenzyme composition.

In general, according to the present inventions NADH or other reduced dinucleotides are stabilized in the present invention by treating propylene glycol with a 4 Angstrom molecular sieve and with sodium borohydride to eliminate small oxidants from the solution. The treated propylene glycol is mixed 1:1 with a buffer containing boric acid and adjusted to pH 10.0. The NADH or reduced analogs of NADH are readily soluble in the aqueous-based material. This solution may be stored for at least about one year in plastic or glass storage devices. The NADH solution may be re-used many times and does not suffer any loss upon opening the container.

The boronate anion is believed to bind dinucleotides by binding to the 1,2-cis diol at the 2′,3′ position of ribose. For this reason, boric acid and its salts and borate derivatives of boric acid and their salts may generally be referred to as cis-hydroxyl binding compounds. See e.g., Fulton, "Boronate Ligands in Biochemical Seaprations", Amicon Corporation, Scietific Systems Division, Danvers, Massachusetts (1981). Borate derivates of boric acid which may be useful according to the present invention include phenyl boronate, alkane boronates, 2-phenylethane boronates, 3-aminobenzene boronic acid and other boronate esters. See e.g. the following publications incorporated by reference herein: Fulton, supra; Glad et al., *J. Chromatogr.*, 200, 254–260 (1980) and Bouriotis et al., *J. Chromatogr.*, 210, 267–278 (1981). The presence of more than one accessible 1,2-cis-diol in NAD(H), NADP(H), and FAD($H_2$) may contribute to a tight binding with borate, although hydrogen bonding and hydrophobic effects may also play a part. Fulton, supra.

Although it is not intended that the present invention be limited to any particular mode of action, it is believed that binding of borate to the cis-hydroxyls of the dinucleotide blocks nucleophilic attacks by these hydroxyls on adjacent labile linkages. Such nucleophilic attack may result in degradation of the molecule into mononucleotides.

Propylene glycol is used according to the present invention to minimize the interaction of water with the reduced pyridinium compound and to thereby minimize oxidation. By lowering the dielectric constant of the solution it is believed to render NADH more stable.

A Bicine buffer is used to keep the pH of the solution between about 8 to about 11. NADH is more stable at high pH especially above pH 8.0. Lowry et al., *J. Biol. Chem.*, 236, 2756–2759 (1961); and Wu et al., *Clin. Chem.*, 32, 314–319 (1986). A high pH is generally believed to maintain the dinucleotide in a reduced state and to prevent the loss of borate. Sodium borhydride is used to treat propylene glycol at about 200 mg/l overnight. This treatment minimizes oxidants found in solution. Upon reaction, $H_2O$, boric acid and $H_2$ are formed. Although sodium borohydride is presently preferred, it is anticipated that other borohydride salts which upon breaking down form boric acid will be useful as well.

A 4 Angstrom molecular sieve is used to clean up propylene glycol pulling out water, oxidants, such as aldehydes and peroxy compounds, and other contaminants.

The present invention is illustrated in more detail in the following examples. In Example 1, canned propylene glycol, suspected of metal contamination, is treated to improve its perfomance which is compared with the performance of bottled propylene glycol. Pure propylene glycol compositions are also compared with aqueous solutions in Example 1. Example 2 provides a comparison of NADH compositions according to the present invention at various pH values and a determination of an optimal pH for the stability of NADH solutions. In Example 3, the shelf life of a presently preferred embodiment of the present invention is examined. In Examples 4 and 5, the stability of the present invention when combined with blood urea nitrogen (BUN) reagents or with triglyceride assay reagents, respectively, is described. Example 6 concerns a mixed reagent employing the stabilized composition according to the present invention in materials for a a determination of blood ammonia. In Example 7, the stabilized composition according to the present invention is examined for suitability in an automated BUN assay. In Example 8, the dinucleotide compositon according to the present invention is considered for application in an alanine transaminase assay. Example 9 describes the use of the stabilized composition according to the present invention in an aspartase aminotransferase assay. Example 10 concerns the use of an NADPH solution according to the present invention.

EXAMPLE 1

In order to investigate the effect of varying pH, to compare the use of propylene glycol treated to remove various contaminants versus untreated propylene glycol and to compare the use of "pure" propylene glycol with the use of aqueous mixtures, the following experiments were performed.

Eight different experimental conditions were divided among 3 groups: Group I, untreated propylene glycol; Group II, treated propylene glycol; and Group III 50% solution propylene glycol.

In Group I there were four samples: (1) propylene glycol from a metal can plus 22 mg/ml NADH; (2) bottled propylene glycol at pH 8.4 with 22 mg/ml NADH; (3) bottled propylene glycol at pH 10.3 with 22 mg/ml NADH; and (4) bottled propylene glycol at pH 11.8 with 22 mg/ml NADH.

In Group II these were three samples: (5) number (2) from Group I above treated with NaBH$_4$ plus 22 mg/ml NADH; (6) number (2) from Group I above treated with NaBH$_4$ and Chelex Resin 5% w/v (Sigma Chemical Co., St. Louis, Missouri) plus 22 mg/ml NADH; and (7) number (2) from Group I above only treated with a molecular sieve 3% w/v, 8–12 mesh (Davison Chemical Division, Baltimore, Maryland).

In Group III there was a single sample, (8), which contained: 50% bottled propylene glycol, 100 mM Bicine, and 50 mM boric acid at pH 8.4; and 11 mg/ml of NADH.

The NADH solutions were used as a sample in a reaction mixture containing tetrazolium salt (INT) diaphorase. The amount of NADH remaining at the end of a sampling interval was porportional to the amount of formazan-INT formed by the following reaction.

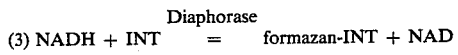
(3) NADH + INT $\xrightarrow{\text{Diaphorase}}$ formazan-INT + NAD

That is, the more NADH present in the tested solution, the more formazan present in the result.

Figure 2:
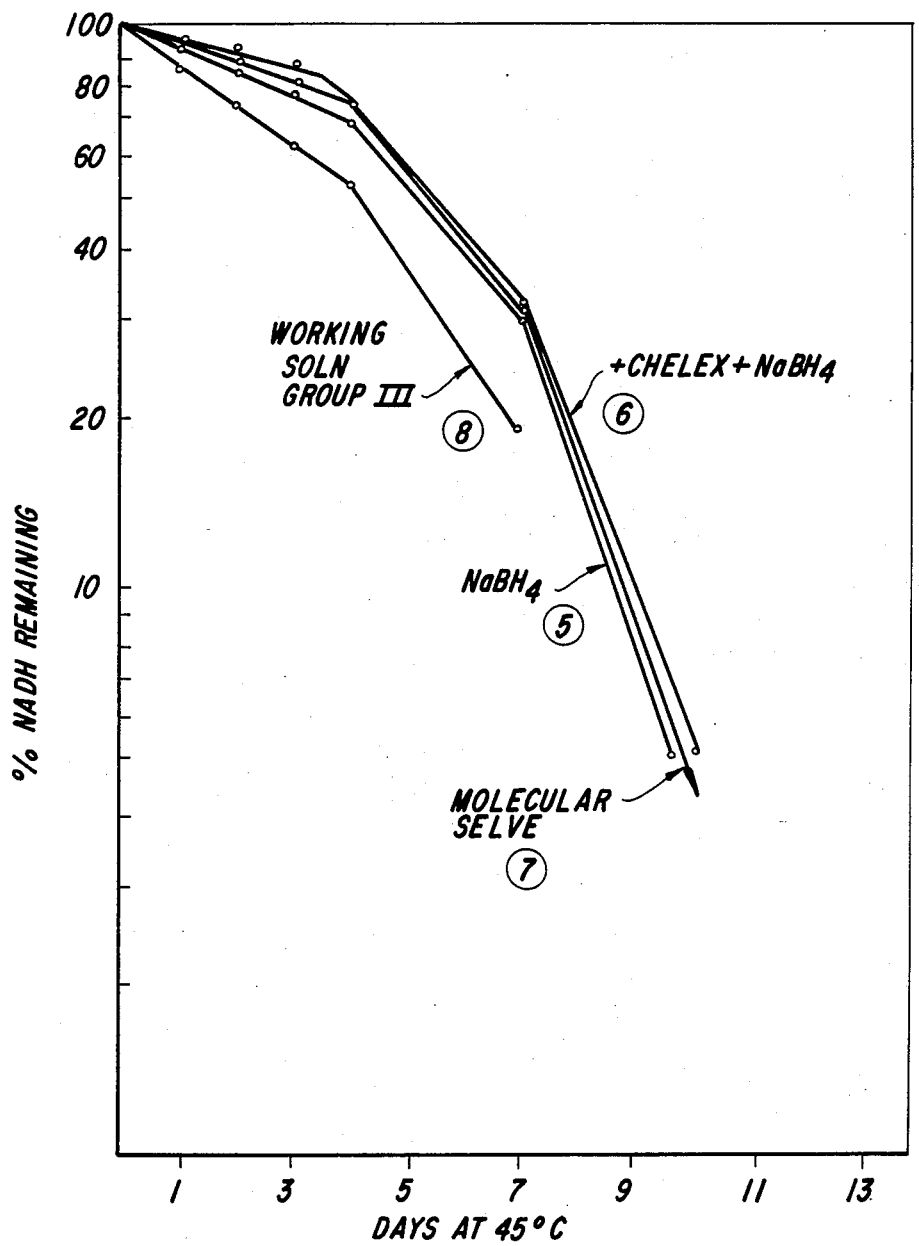
FIG. 2 is a graphic depiction of the stability of NADH in propylene glycol solutions which had undergone various purification procedures.

All NADH samples were stored at 45° C. for a sampling interval equal to the number of days indicated in FIGS. 1 and 2.

On the basis of the results of this experiment, as illustrated in FIGS. 1 and 2, canned propylene glycol samples where determined to be very unstable. Also, the solution at pH 8.4 was determined to be less stable than the solution at pH 10.3 which was determined to be less stable than the solution at pH 11.8, although NADH solutions under these conditions were at best are only 75% stable after 14 days. It was also concluded that, for contaminated propylene glycol, increased stability is obtained by treatment with sodium borhydride and a molecular sieve, while Chelex Resin did not help.

EXAMPLE 2

An experiment was performed to investigate NADH stability in a 50% v/v solution in water at various values of pH for comparison with the results for "pure" propylene glycol as described above. The assay procedure in Example 1 was used.

Figure 3:
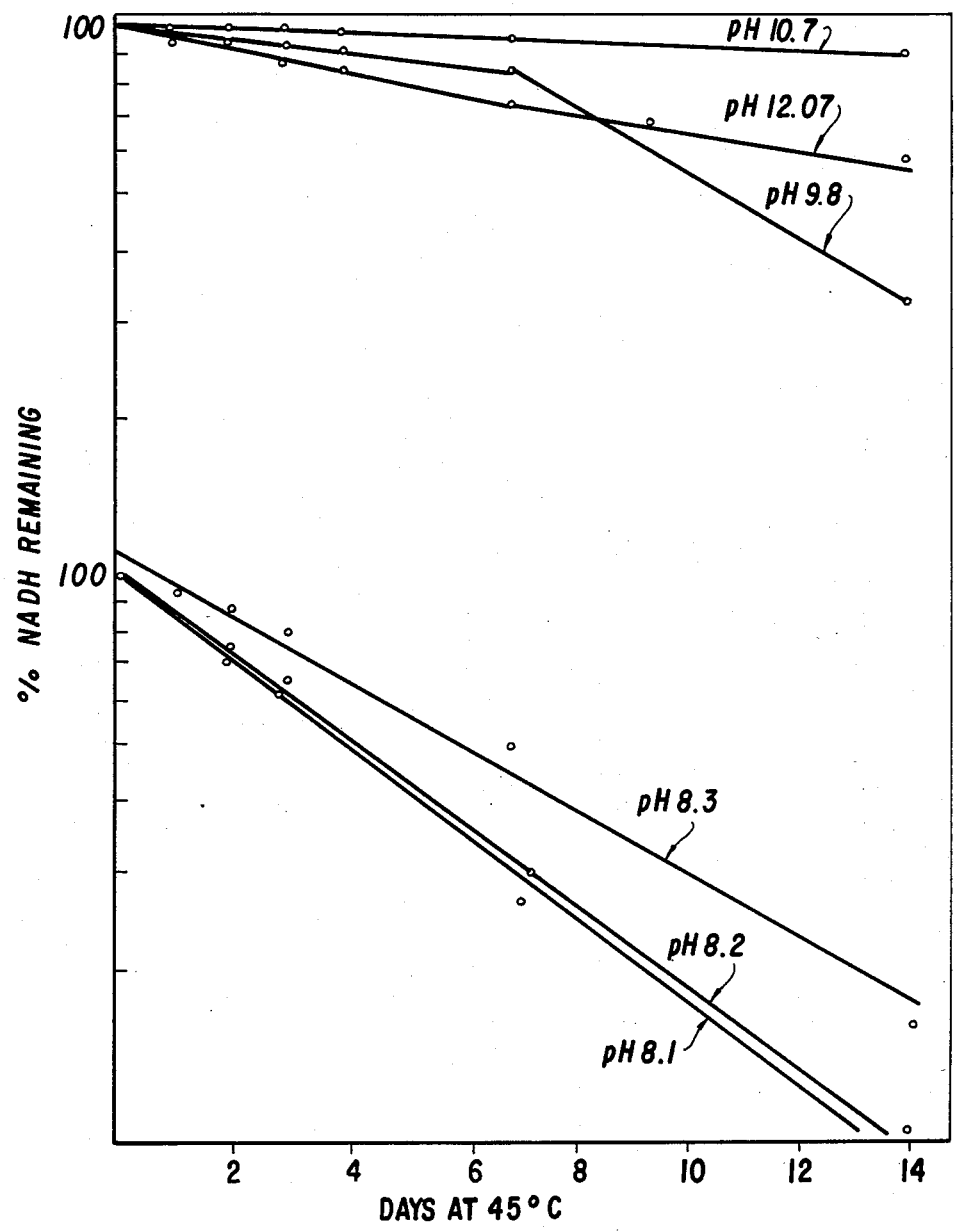
FIG. 3 is a graphic depiction of a comparison of the stability of NADH in pure propylene glycol with the stability in 50% v/v propylene glycol/water at various pH values.

The results presented in FIG. 3 indicate that "pure" propylene glycol compositions at different pH values, as illustrated in the top three lines of FIG. 3, are more stable than 50% solutions, represented by the bottom three lines of FIG. 3, when the pH is 8.3 or less.

EXAMPLE 3

A preferred dinucleotide stabilizing solution was made by treating propylene glycol with a 4 Angstrom molecular sieve at 4% w/v and adding sodium borohydride at 2 mg/ml. The solution was stored in a vented system overnight, or at least for 8 hours. A distilled water solution of 200 mM Bicine and 100 mM boric acid at pH 9 was prepared. This solution was mixed 1:1 with the propylene glycol so the final concentrations are: 50% propylene glycol; 50 mM boric acid; and 100 mM Bicine. The pH was adjusted to 10 with NaOH. Approximately 11 mg/ml of NADH were slowly added. This solution is hereinafter referred to as the dinucleotide solution. When stored unmixed at 2°–8° C., this solution was at least stable for about one year. Typical stabilities are: about 1 year at −20° C.; about 1 year at 2°–8° C.; 2 months at room temperature; 1 month at 37° C; 2 weeks at 45° C. This solution may be mixed with enzyme solutions for the determination of clinical analytes.

Figure 4:
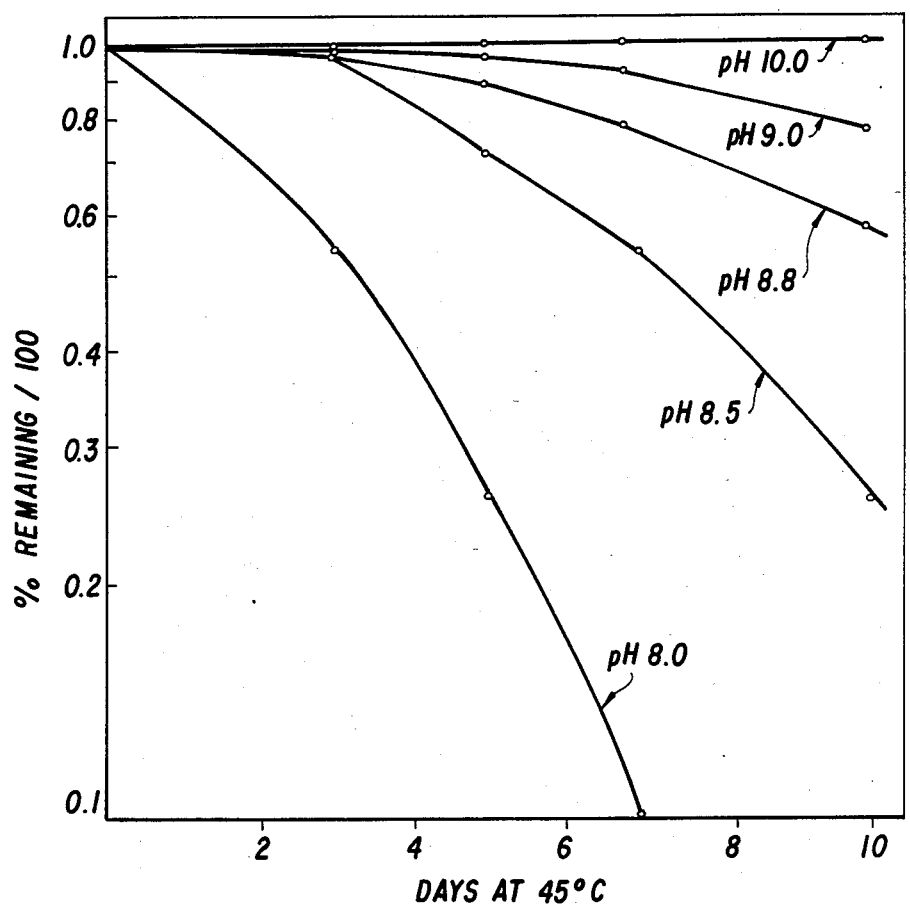
FIG. 4 is a graphic depiction of the results of a determination of an optimal pH for a stabilized dinucleotide solution according to the present invention.

As illustrated in FIG. 4, a stability test of the preferred dinucleotide solution was run at the elevated temperature of 45 degrees C. to simulate the effects of prolonged storage at lower temperatures. The results as presented in FIG. 4 suggest that a pH of about 10 is optimal for solutions according to the present invention which may be stored before use.

Currently preferred components for the dinucleotide solution according to this Example include: Bicine (#B-3876 as available from Sigma Chemical Co., St. Louis, Missouri); NADH (#N-8129 as available from Sigma Chemical Co.); sodium borohydride (#S-9125 as available from Sigma Chemical Co.); propylene glycol (food grade as available from Dow Chemical Co., Midland, Michigan) and boric acid (as available from Baker Chemical Company).

EXAMPLE 4

The dinucleotide solution of Example 3 may be used to determine a sample of BUN when combined with a solution of 20 U/ml urease and 5 U/ml glutamate dehydrogease diluted 1:80 with 0.2 mg/ml alpha ketoglutarate in 15 mM Tris buffer at pH 8.3. If the solution contains 0.1% sodium azide, the combined reagent may be used to determine BUN concentration for up to three months. After three months, such a combined assay reagent system lost only 15% of the original linearity claim of 150 mg/l.

EXAMPLE 5

The dinucleotide solution of Example 3 may be used to determine the concentration of triglycerides in a sample when mixed 1:80 with a buffered solution containing 100 U/ml lipase, 5 U/ml glycerol kinase, 2 U/ml pyruvate kinase 1 U/ml lactate dehydrogenase; 0.7 mM phosphoenol pyruvate; 0.05 mM ATP; and 10 mM MgCl$_2$. When combined, the solution may be used to determine triglycerides in a sample for up to 1 month.

EXAMPLE 6

Ammonia determinations in serum are toxicologically important. Most major hospitals perform several ammonia tests a month. However, because of the length of the interval between requests for this test there is a need to have reagents which are relatively stable. The dinucleotide solution of Example 3 may be mixed 1:80 with an ammonia-free solution containing 10 U/ml glutamate dehydrogenase and 0.5 mg/ml alpha ketoglutarate in Tris buffer at pH 8.5, and may readily be used to determine ammonia levels in serum. This solution unmixed is stable at least for up to about 1 year. When mixed it is stable for at least 1 month.

EXAMPLE 7

BUN may also be determined flurometrically by the use of reagents in the Radiative Attenuation Assay, the subject of commonly owned U.S. Pat. No. 4,495,293 which is incorporated by reference herein. In this assay, the reagents may be split among 3 bottles. The reagents may be dispensed from: a bottle #1 containing NADH solution: a bottle #2 containing 1600 U/ml urease, 16 mg/ml alpha ketoglutarate and 400 U/ml glutamate dehydrogenase in a phosphate buffer at pH 7 and 25% glycerol plus $5 \times 10^{-6}$ mg/l sodium fluorescein; and bottle 3 containing medola blue 0.5 mg/ml, 10 mg/ml thiazoyl blue and citrate buffer pH 2.5.

When bottles 1 and 2 are mixed 1:1:40 with 100 mM phosphate buffer at pH 7.5 a blood sample is hydrolyzed and produced ammonia is reductively assimilated in glutamate with a concomimant loss in NADH. In a second reaction remaining NADH may be reacted with bottle 3 in 1:40 dilution with said buffer to catalytically form MTT-formazan. The amount of MTT-formazan produced is proportional to the amount of BUN in original sample. This reagent system typically yields CVs of less then 6% with clinical samples. A combination of bottles 1,2 and 3 may be used to detect BUN in samples for a least about 1 year.

EXAMPLE 8

Alanine transaminase (ALT) may also be determined by using the dinucleotide solution of Example 3, 500 mM L-alanine, 15 mM alpha ketogutarate, 0.1 mM pyridoxal-5-phosphate (optional), and 600 U/l lactate dehydrogenase. This mixture when combined is stable for at least 1 month and may be used to quanitatively measure ALT in serum or plasma.

EXAMPLE 9

Aspartate Aminotransferase (AST) may be measured by using the dinucleotide solution of Example 3 in combination with 240 mM L-aspartate, 12 mM alpha ketoglutarate, 0.10 mM pyridoxal-5-phosphate, 420 U/l malate dehydrogenase, and 600 U/l Lactate dehydrogenase. This mixture is stable for at least 1 month and may be used to quanitatively measure AST in serum or in plasma.

EXAMPLE 10

In the dinucleotide solution of Example 3 NADH may be replaced with NADPH. Certain enzymes in diagonastic tests utilize NADPH instead of NADH. The glutamate dehydrogenase purified from a Proteus sp. utilizes only NADPH. This enzyme may be used to replace the glutamate dehydrogenase enzyme in Example 2 for the determination of BUN.

Although the present invention has been described in terms of a preferred embodiment, it is understood that modifications and improvements of the present invention will occur to those skilled in the art. For example, although the present invention has primarily been exemplified by stabilized solutions of NADH, solutions of other dinucleotides may be stabilized according to the present invention. For example, it is contemplated that NADPH, reduced 3-acetyl pyridine adenine dinucleotide, reduced 3-acetyl pyridine adenine dinucleotide phosphate, reduced thionicotinamide adenine dinucleotide, reduced thionicotinamide adenine dinucleotide phosphate, and reduced nicotinamide hypoxantine dinucleotide may also be stabilized according to the present invention.

Similarly, although a Bicine buffer has been employed in the Examples above, it is contemplated that any buffer with a $pK_a$ and a buffer capacity sufficient to maintain a dinucleotide solution within the preferred pH range may be employed. For example, other suitable buffers include: Tris [Tris (hydroxy-methyl) aminomethane]; Hepes [4-(2-hydroxylethyl)-1-piperazine ethane sulfonic acid]; triethanolamine; MOPS [4-morpholine propane-sulfonic acid]; CHES [2-(cyclohexylamino) ethane-sulfonic acid]; and CAPS [3-cyclohexylamino-1-propane sulfonic acid].

Other assays in which the coenzyme composition according to the present invention may be useful include assays involving lactic dehydrogenase pyruvate to lactate [i.e. LDH (P to L)], and uric acid.

In addition, it is contemplated that other stable organic solvents which are miscible with water may be employed in the present invention in place of propylene glycol as long as they do not react with reduced dinucleotides other than by forming hydrogen bonds. Liquid polyols having from 2 to 4 hydroxyl groups and 2 to 10 carbon atoms are preferred. These preferred polyols include glycerol and 1,2-propanediol.

It should also be taken into account that the coenzyme composition according to the present invention may be made up in a concentrated form and diluted for use.

Therefore, it is intended that the present invention include all such variations as come within the scope of the invention as claimed.

I claim:

1. A stabilized coenzyme composition comprising:
   a basic, aqueous solution;
   a reduced dinucleotide at a first concentration in said aqueous solution;
   a polyhydroxyl alkyl solvent in said aqueous solution; and
   a borate cis-hydroxyl binding compound at a second concentration in said aqueous solution, said second concentration being about equal to or greater than said first concentration.

2. The coenzyme composition as recited in claim 1 wherein said polyhydroxyl alkyl solvent is at a concentration within a range of about 20% v/v to about 90% v/v of said aqueous solution.

3. The coenzyme composition as recited in claim 2 wherein said aqueous solution comprises a buffer effective to maintain said aqueous solution at a pH of greater than 8.0.

4. The coenzyme composition as recited in claim 3 wherein said borate, cis-hydroxyl binding compound is selected from the group consisting of: boric acid; salts of boric acid; borate derivatives of boric acid; and salts of borate derivatives of boric acid.

5. The composition as recited in claim 4 wherein said polyhydroxyl alkyl solvent is propylene glycol.

6. The composition as recited in claim 5 wherein said pH of said aqueous solution is between about 8 and about 11.

7. The composition as recited in claim 6 wherein said second concentration is between about 10 and about 50 mM.

8. The composition as recited in claim 7 wherein said concentration of said polyhydroxyl alkyl solvent is approximately equal to 50% v/v of said aqueous solution.

9. The coenzyme composition as recited in claim 8 wherein said reduced dinucleotide is selected from the group consisting of a reduced pyridine dinucleotide and a reduced pyridine dinucleotide phosphate.

10. The coenzyme composition as recited in claim 9 wherein said reduced dinucleotide is NADH and wherein said first concentration is between within a range from about 0.001 mM to about 50 mM.

11. The coenzyme composition as recited in claim 9 wherein said borate cis-hydroxyl binding compound is boric acid, wherein said second concentration is at least equal to said first concentration and is within a range from about 10 mM to about 500 mM.

12. A stabilized coenzyme composition comprising:
an aqueous solution at a pH between about 8 and about 11;
NADH at a concentration within a range from about 0.001 mM to about 50 mM.
boric acid at a concentration at least equal to said concentration of NADH and within a range from about 10 mM to about 500 mM; and propylene glycol at a concentration within a range from about 20% v/v to about 90% v/v of said aqueous solution.

13. The coenzyme composition as recited in claim 12 further comprising a Bicine buffer at a concentration within a range from about 10 mM to about 500 mM.

14. The coenzyme composition as recited in claim 13 wherein said NADH is at a concentration of 10 mM, said boric acid is at a concentration of 50 mM, said propylene glycol is at a concentration of 50% v/v, and said Bicine buffer is at a concentration of 200 mM, and is adjusted to pH 10.0.

15. A method for stabilizing a solution of a reduced dinucleotide comprising the steps of:
dissolving a first concentration of a reduced dinucleotide in a basic aqueous solution;
buffering the aqueous solution to a pH between about 8.0 and about 11.0;
exposing the reduced dinucleotide to a borate cis-hydroxyl binding compound at a second concentration about equal to or greater than the first concentration; and
reducing exposure of the reduced dinucleotide to water by making the aqueous solution about 20% v/v to about 90% v/v in a polyhydroxyl alkyl solvent.

* * * * *